(12) United States Patent
Villaverde Fernandez et al.

(10) Patent No.: US 8,242,053 B2
(45) Date of Patent: Aug. 14, 2012

(54) BIOLOGICAL FERTILIZER, METHOD FOR OBTAINING SAME AND USE THEREOF AS A PLANT GROWTH STIMULATOR

(75) Inventors: Mario Jorge Villaverde Fernandez, Murcia (ES); Ana Isabel Fernández Martínez, Murcia (ES); Juan Antonio Casanova Roca, Santomera (ES); Jorge Malo López-Roman, Murcia (ES); José Antonio Nicolás Martínez, Murcia (ES); Isidro Blanca Picó, Murcia (ES); Antonio García Gómez, Murcia (ES); Pedro Martínez Ortiz, Murcia (ES)

(73) Assignee: Probelte, S.A., Espinardo (ES)

( * ) Notice: Subject to any disclaimer, the term of this patent is extended or adjusted under 35 U.S.C. 154(b) by 51 days.

(21) Appl. No.: 12/675,863

(22) PCT Filed: Aug. 27, 2007

(86) PCT No.: PCT/ES2007/000497
§ 371 (c)(1),
(2), (4) Date: Aug. 31, 2010

(87) PCT Pub. No.: WO2009/027544
PCT Pub. Date: Mar. 5, 2009

(65) Prior Publication Data
US 2011/0045976 A1    Feb. 24, 2011

(51) Int. Cl.
*A01N 59/04*    (2006.01)
*C05F 11/08*    (2006.01)

(52) U.S. Cl. ............................................. 504/101; 71/6
(58) Field of Classification Search ..................... None
See application file for complete search history.

(56) References Cited

U.S. PATENT DOCUMENTS

| 570,813 | A | 11/1896 | Nobbe et al. |
| 1,212,196 | A | 1/1917 | Earp-Thomas |
| 4,670,037 | A | 6/1987 | Kistner, Sr. |
| 5,366,532 | A | 11/1994 | Fages et al. |
| 5,951,978 | A | 9/1999 | Red'kina |
| 6,596,273 | B2 | 7/2003 | Cheung |

FOREIGN PATENT DOCUMENTS

| ES | 2 093 559 | 12/1996 |
| ES | 2 234 417 | 6/2005 |
| ES | 2234417 A1 * | 6/2005 |

OTHER PUBLICATIONS

International Search Report for PCT International Patent Application PCT/ES2007/000497 mailed May 22, 2008.

* cited by examiner

*Primary Examiner* — Alton Pryor
(74) *Attorney, Agent, or Firm* — RatnerPrestia

(57) ABSTRACT

A biological fertilizer and plant growth stimulator including: a. a pure culture of strain $C_3$ of the *Pantoea dispersa* species deposited in the Spanish Type Culture Collection (CECT) with CECT number 5801, b. a pure culture of strain M3 of the *Azospirillum brasilense* species deposited in the CECT with CECT number 5802, both immobilized in a solid support acting as a slow release system, and c. indole-3-acetic acid, and a method for preparing the biological fertilizer and the use thereof as a plant growth stimulator.

22 Claims, 2 Drawing Sheets

Figure 1 – Stability test of the product at room temperature
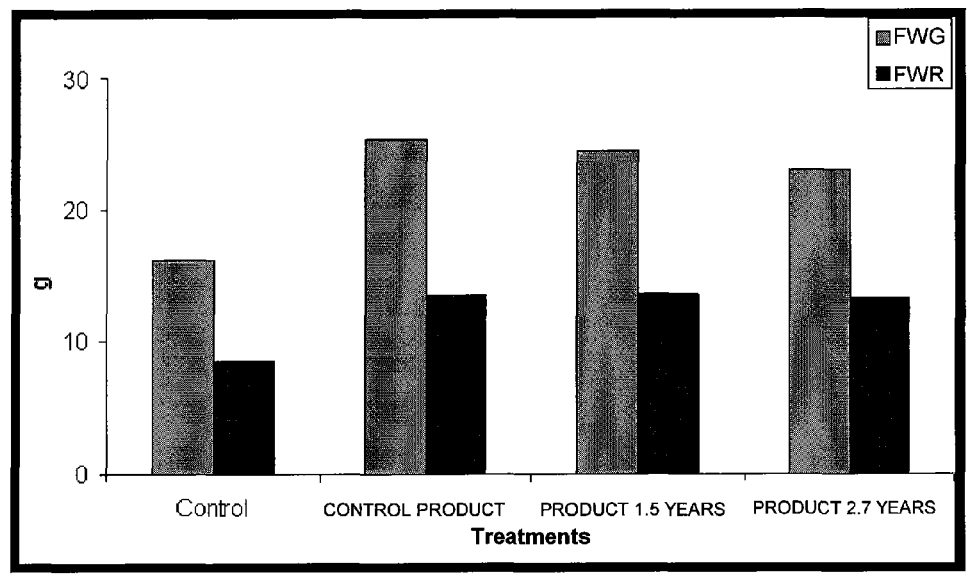
Figure 2 – Mean Weight of the lettuce in each of the tests conducted
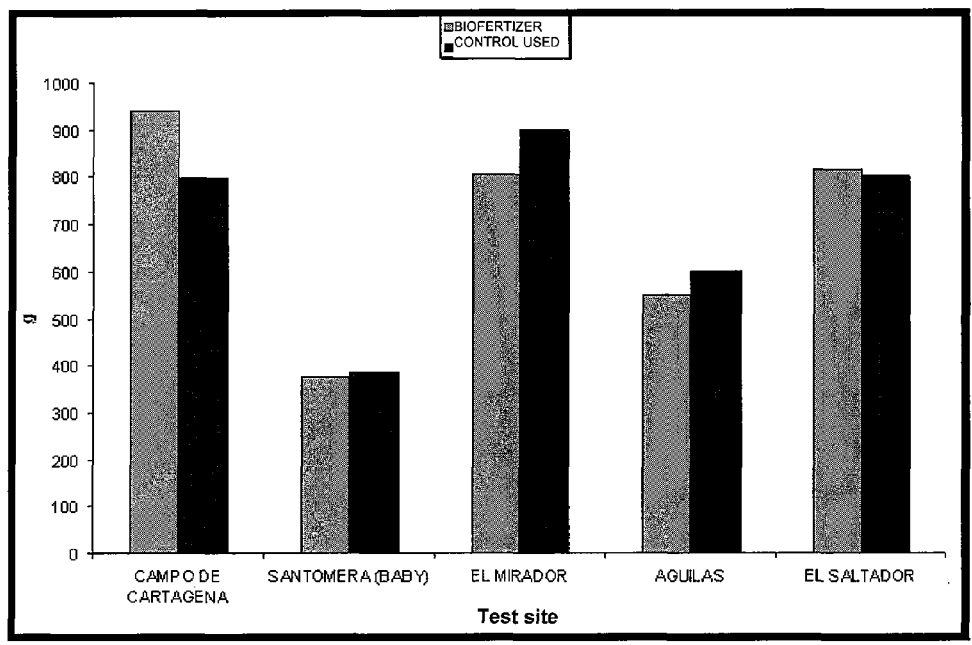

Figure 3 – Amount of nitrates in the soil once the crop harvesting has ended
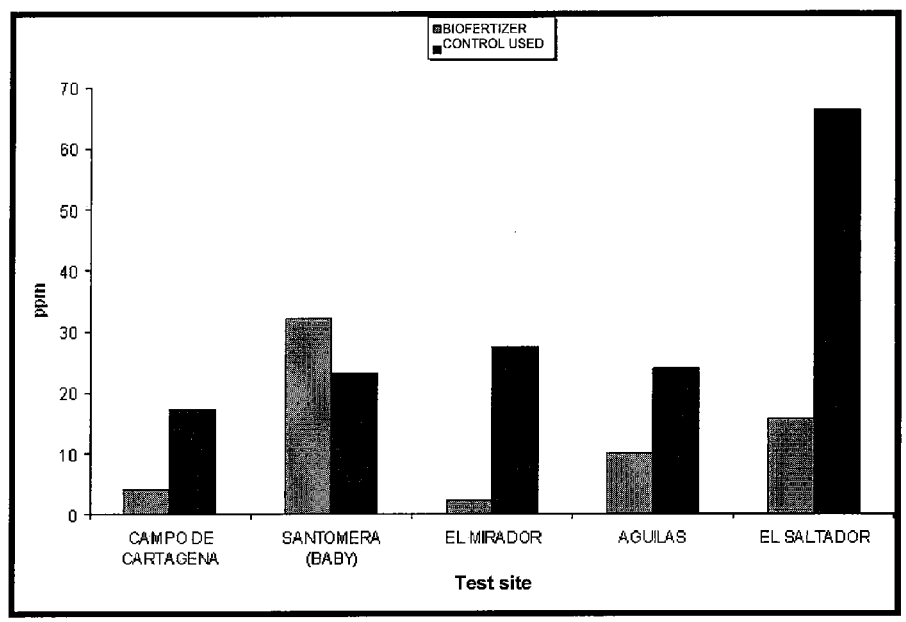
Figure 4 – Nitrate content in the leaf at the time of harvest
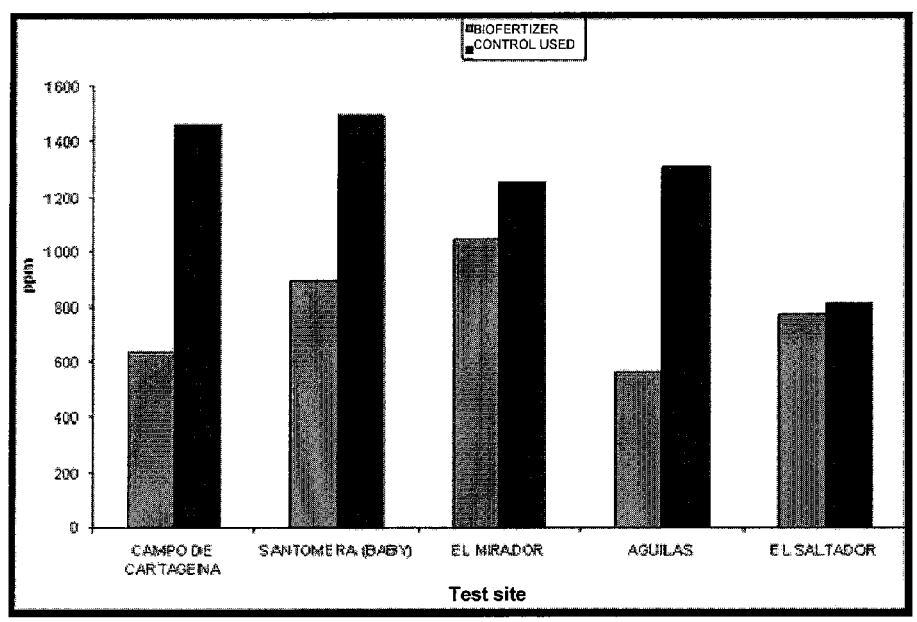

BIOLOGICAL FERTILIZER, METHOD FOR OBTAINING SAME AND USE THEREOF AS A PLANT GROWTH STIMULATOR

This application is a U.S. National Phase Application of International Application No. PCT/ES2007/000497, filed Aug. 27, 2007.

FIELD OF THE INVENTION

The present invention relates to a product for biological fertilization consisting of a granulated formulation comprising two strains of bacteria of the *Azospirillum* and *Pantoea* genera, with capacity to fix atmospheric nitrogen, to solubilize phosphates as well as other mineral nutrients of the soil and to produce large amounts of plant growth stimulating substances. Said microorganisms have been immobilized by means of the technique of adsorption to a solid support, acting as a slow release system, which furthermore assures high stability in cell viability, as well as sufficient organic nutrients and salts to facilitate the colonization of the roots of the plants. The isolated microorganisms, the method of cell immobilization, and the use of the biological fertilizer thus obtained as a plant growth stimulator are also object of this invention.

STATE OF THE ART

The use of fertilizers is essential for maintaining high crop yields. Important amounts of nitrogen, phosphorus and potassium, as well as other mineral elements, are added to the soil by means of chemical fertilization, however, the availabilities of these elements are very low since it is well known that a fraction is immobilized in the soil, forming insoluble compounds that cannot be assimilated by the plants and another fraction is washed out by means of a leaching process, which generates a considerable environmental pollution problem in addition to economic losses.

In the case of phosphorus, particularly a considerable part of the soluble phosphates added is insolubilized by the iron and the aluminum in acid soils and by the calcium in calcareous soils (Chabot et al., 1993), being progressively converted into less assimilable forms. As a result of the various retention mechanisms, most of the phosphorus applied by means of fertilization cannot be used by the crops and is retained in the soil in insoluble form (Stevenson, 1986). Given this phenomenon and the cyclic application of fertilizers, the concentration of phosphorus in the soil has considerably increased, so long-term crops could be established in many soils if these reserves could be exploited economically (Kucey et al., 1989).

The importance of microorganisms in the cycle of nutrients in the soil and their role in plant nutrition is well known. Their active participation in decomposition and mineralization of organic matter, as well as in the fixation and release of nutrients of the soil is crucial for maintaining plant productivity. The interactions occurring between the microorganisms of the soil and the roots of the plants meet important nutritional requirements for both. The roots are directly influenced by the composition and density of the microbial community that is developed in such roots, this being known as the "rhizosphere effect", which can be estimated but it is known that it particularly depends on the plant and its physiological maturity (Atlas, R. M. and Bartha, R., 1993) The practice of inoculating plants with microorganisms has been well known for many years (U.S. Pat. No. 570,813).

A group of microorganisms having considerable importance in this phenomenon is that which participates in solubilizing the phosphorus from sources that would otherwise be inaccessible for plants (Kucey et al., 1989).

Phosphate solubilizing microorganisms have been isolated in virtually all the tested soils, although the number and proportion thereof varies according to the type of soil, the climate and other factors such as the historic evolution of the soil. Many microorganisms are capable of assimilating the insoluble phosphorus of the soil, releasing part of it in the form of soluble phosphates which can in turn be used by the plants, thus contributing to plant nutrition (Chabot et al., 1993). It is generally accepted that the solubilization of phosphates in soil is due to the production of organic acids and chelating oxo acids from sugars (Leyval and Barthelin 1989, Deubel and Gransee 1996, Yadav and Dadarwal, 1997).

The *Enterobacter* and *Pantoea* genera have been used in agriculture as phosphate solubilizers and for protection against plant diseases. Among these genera, *Pantoea dispersa* is a species that has been used for these purposes.

Another aspect which plays a very important role in practice is the use of microorganisms of the rhizosphere that are atmospheric nitrogen fixers. This practice has also been known for many years (U.S. Pat. No. 1,212,196). A number of microorganisms have been used for this function, including bacteria of the genera such as *Rhizobium, Azotobacter* and *Azospirillum* (Spanish patent ES2093559; U.S. Pat. No. 5,951,978), and fungi of the *Saccharomyces, Hansenula* (U.S. Pat. No. 6,596,273) and *Aspergillus* (U.S. Pat. No. 4,670,037) genera, among others.

Nitrogen is an abundant element, making up almost 80% of the Earth's atmosphere and a very scarce nutritive part. The paradox is easily solved: atmospheric nitrogen is inert and most organisms cannot use it, only being incorporated in biological syntheses when it has been "fixed" or combined with certain elements such as hydrogen or oxygen. Bacteria are capable of fixing $1.5 \times 10^8$ metric tons per year, a considerable part of which is synthesized by means of the Haber-Bosch process (Brill, W. F., 1977; Atlas and Bartha, 1993).

Several experiments conducted in Brazil in the 1970s determined the significant contribution of fixed $N_2$ for plants by different microorganisms, *Azospirillum* being among the main microorganisms (Döbereiner and Day, 1976; Neyra and Döbereiner, 1977, inter alia).

It is known that different plants species have different effects on the rhizosphere, it also being known that the isolated strains in a type of plant species have a completely different effect on the rhizosphere from which it was isolated with respect to other crops. However, in their work with *Azospirillum brasilense*, Basham and Levanony (1988) concluded that such species is capable of colonizing plants of different species by being adsorbed to the roots.

The use of this genus in the production of biological fertilizers is very common today (U.S. Pat. Nos. 5,366,532 and 5,951,978 and Spanish patent ES2093559)

Current trends in inoculating plants with microorganisms are aimed at using mixed cultures (also called consortia) which enhance phenomena such as the increase of the efficiency of the absorption of the phosphorus by the roots, the biological fixation of nitrogen, plant growth stimulation by the production of plant growth regulating substances, as well as siderophores, and protection against diseases caused by pathogenic microorganisms, among others. This practice has been shown to be the most effective in biofertilization.

The physical form of a biostimulator is also a determining factor in the practical result of the prepared product and can vary, provided that it is compatible with agricultural practices, being readily incorporated in routine operations. The microorganisms must remain viable in the product, either in latent state or metabolically active. This factor has two determining aspects, the durability of the product and the capacity of the product to colonize the roots of the crops that are to be stimulated or protected, once applied in the field. Some problems may arise when dealing with cells that do not have the capacity to form resistant structures since the cultures gradually lose viability over time and their survival capacity in the soil is furthermore very low. For this reason, it is essential for the product to be capable of preserving cell viability in adverse conditions for long periods of time and assuring, as much as possible, the capacity to colonize the roots once applied in the field. One of the most important criteria to take into account for this purpose is to achieve preparations which consistently release a considerable number of viable cells. For this purpose, cell immobilization techniques offer a series of advantages with respect to free cells, making them very appealing for their application in practice and quite particularly for agricultural and environmental biotechnology. The use of immobilized cells can enhance the effects of microorganisms without creating pollution problems, giving rise to very active and novel products. A widely used technique in practice is adsorption. There are a number of supports used for this purpose. In agriculture in particular, the use of clay, vermiculite, perlite, sepiolite, kaolin, diatomaceous earth, natural zeolites and the like is typical.

Zeolites are aluminosilicates, the networks of which are formed by $AlO_4^-$ and $SiO_4^-$ tetrahedrons. This framework has a negative charge which is compensated with exchangeable cations occupying specific sites in the channels and cavities of the zeolite. This salt has two very important properties: the capacity of adsorption and ion exchange, which are very advantageous for its possible use as an immobilization support. The properties of these products could be very appealing for obtaining a dry product for biofertilization, even more so if it involves microorganisms which are not capable of forming resistant structures. For this purpose, it would be essential for cell death to be very low or nil during the production process and particularly in the step of drying the product. Achieving this objective would allow obtaining very effective products provided that a production process is achieved.

ES 2 234 417 describes a biological fertilizer consisting of a granular formulation containing strain $C_3$ of the *Pantoea dispersa* species deposited in the Spanish Type Culture Collection (CECT) with CECT number-5801 and strain $M_3$ of the *Azospirillum brasilense* species deposited in the Spanish Type Culture Collection (CECT) with CECT number-5802, both immobilized in a solid support and a process for the preparation thereof.

Said biological fertilizer is capable of fixing atmospheric nitrogen, as well as solubilizing phosphates and other mineral nutrients, thus having good fertilizing activity. This activity is due to the fact that, for example, strain $C_3$ is capable of producing large amounts of organic acids, mainly gluconic acid, which is useful for solubilizing the insoluble phosphate of the soil, while for example strain $M_3$ is capable of fixing nitrogen and producing indole-3-acetic acid, which is a very important factor involved in plant growth.

These strains are immobilized in a solid support, for example zeolite, in order to obtain an end product characterized by good stability as well as satisfactory cell viability. The solid support is additionally supplied with salts to facilitate colonization of the roots of the plants.

However, when the fertilizer according to ES 2 234 417 contacts with the plant through the soil, it needs some time to performing its action since in order for the strains to be able to begin their activity, they must colonize the roots of the plants and establish with said roots a relationship which allows them to perform their action of conversion into a useful product. Thus, the fertilizing activity cannot be carried out immediately when the fertilizer contacts with the plant through the soil, but it can be observed after a certain time, depending on the characteristics of the soil, on the climatic conditions and on many other factors. This aspect can cause a delay in the biofertilizing action and a certain delay in growth, at least initially, in the treated plants. In fact, certain climatic conditions such as rain, hail, etc., can partially or completely affect the fertilizer of the soil, therefore disabling its activity.

Furthermore, according to ES 2 234 417 the process for preparing a biological fertilizer includes the adsorption of the strains as well as of the nutrients and salts in the solid support, thus obtaining a wet product which needs to be dried in order to obtain high cell stability. In fact, a high moisture level in the end product can cause fast degradation of the strains and lower viability.

The step of drying is carried out at a temperature comprised between 60-80° C., which is relatively high for preserving the viability of the strains. The moisture level thus obtained is comprised between 3-6%.

According to ES 2 234 417, each strain as well as the nutrients are adsorbed in a different solid support, thus obtaining at least two different series of solid supports, which are mixed in predetermined amounts, obtaining the biological fertilizer. According to this process, it is therefore necessary to carry out at least two different steps of drying since the nutrients and the strains are dried separately and the cells never reach temperatures of greater than 80° C.

SUMMARY OF THE INVENTION

One object of the present invention is to provide a biological fertilizer exerting a fertilizing and/or stimulating action for immediate plant growth as soon as the fertilizer contacts with the plant through the soil.

Another object of the present invention is to provide a biological fertilizer exerting a fertilizing and/or stimulating activity for the improved growth.

Likewise, another object of the present invention is to provide a biological fertilizer the activity of which is maintained, i.e., it is kept stable in storage conditions, for a long period of time, at least two years.

Finally, another object of the present invention is to provide a process for preparing a biological fertilizer comprising a lower number of steps in comparison with the process according to the state of the art having several industrial advantages.

DESCRIPTION OF THE INVENTION

These and other advantages that will be better explained below are obtained with a fertilizer comprising:

a.—a pure culture of strain $C_3$ of the *Pantoea dispersa* species deposited in the Spanish Type Culture Collection (CECT) with CECT number 5801, b.—a pure culture of strain $M_3$ of the *Azospirillum brasilense* species deposited in the CECT with CECT number 5802, both immobilized in a solid support, c.—indole-3-acetic acid (IAA).

The new biological fertilizer according to the present invention contains *Azospirillum brasilense* cells, strain $M_3$, an atmospheric nitrogen fixer, and it has a high capacity to produce plant growth regulating substances of the indole-3-acetic acid (IAA) type, and *Pantoea dispersa*, strain $C_3$, which is highly efficient in the production of organic acids, mainly gluconic acid, for the solubilization of phosphates and other nutrients of the soil, as well as the capacity to produce, for example, siderophores and plant growth regulating substances. Said microorganisms have been deposited in the Spanish Type Culture Collection (CECT) and assigned accession numbers CECT-5802 for *Azospirillum brasilense* $M_3$ and CECT-5801 for *Pantoea dispersa* $C_3$. Said biological fertilizer consists of a product formed by a solid support, in which the bacteria have been immobilized and furthermore containing the nutrients necessary for assuring their survival, once the plants are inoculated, acting as a slow release system.

The microorganism *Azospirillum brasilense* $M_3$ CECT 5802 was obtained by means of a method which combines the isolation in semisolid NFb medium and the selection through its capacity to stimulate the plant growth and produce indole-3-acetic acid and other plant hormones. The capacity to stimulate plant growth was verified by means of laboratory and greenhouse bioassays, according to the methods described by Bashan et al. 1986, Fernández 1995 and Bashan 1998. It was found by means of these bioassays that strain $M_3$ was the one that produced the greatest growth stimulating effect of the more than 50 assayed nitrogen fixing bacteria isolates. The production of indole-3-acetic acid (IAA) was verified by colorimetric (Pilet and Chollet 1970) and HPLC (Olivella et al. 2001) methods, and the presence of other plant hormones of the cytokinin type was also detected. In the production of IAA in tomato medium with 200 $mg \times L^{-1}$ of tryptophan, concentrations of 100-180 $mg \times mL^{-1}$ and a percentage of transformation of up to 95% of this amino acid are achieved. The microorganism *Pantoea dispersa* $C_3$ CECT 5801 was obtained using a method which combines isolation in agar medium with 1N Tris_HCl buffer pH 8, for the sake of the clearance of the agar (Gyaneshwar et al. 1999) and selection by means of determining $PO_4^{3-}$ solubilized in stirred liquid media (Nautiyal 1999), using in both cases insoluble $Ca_3PO_4$ as the only phosphorus source. The organic acids produced were characterized and it was verified that it mainly produces gluconic acid. The selection was also made through the capacity thereof to stimulate plant growth and to produce auxins.

According to the invention, the new biological fertilizer comprises, furthermore of the strains $C_3$ and $M_3$, indole-3-acetic acid (IAA).

This third component represents a significant progress with respect to the known biological fertilizers. In fact, the presence of IAA from the start together with the two strains $C_3$ and $M_3$ gives the resulting product the possibility to be active immediately when the fertilizer contacts with the plant through the soil, since IAA is capable of exerting its action as a plant growth stimulator, whereas strains $C_3$ and $M_3$ are capable of commencing the production of IAA after inoculation thereof in the soil and after the conversion of the necessary substrates. With the new fertilizer according to the present invention, there is an immediate advantage due to the presence of IAA, which acts as a plant growth stimulator as soon as the fertilizer contacts with the plant through the soil, thus allowing strains $C_3$ and $M_3$ to colonize the roots of the plants and to establish therewith the relationship that allows them to perform their growth stimulating action.

Additionally and surprisingly, it has been verified that the same strain $C_3$ produces indole-3-acetic acid (IAA) in a very significant amount.

For example, in the production of IAA in tomato medium with 200 $mg \times L^{-1}$ of tryptophan, concentrations of 80-120 $mg \times mL^{-1}$ and a transformation percentage of up to 60% of this amino acid are achieved.

This is a very important aspect, since the production of indole-3-acetic acid (IAA) from the strain $C_3$ represents an improvement in the total activity of the resulting biological fertilizer.

In fact, in the new product fertilizer according to the present invention, both strains $C_3$ and $M_3$ are capable of producing indole-3-acetic acid (IAA), thus conferring to the product a substantially improved activity as a plant fertilizer and plant growth stimulator if it is compared with known biological fertilizers acting in similar amounts.

The new biological fertilizer according to the present invention in comparison with the same amount of a fertilizer according to the state of the art is thus capable of producing a greater amount of IAA. The aforementioned therefore represents a huge commercial and economic advantage.

According to the present invention, in a first embodiment the IAA can be advantageously produced during the step of fermentation for preparing the strains, or directly added at the end of the strain fermentation process before the adsorption thereof in the solid support. As an alternative, the IAA can be added to the nutrients before the adsorption thereof in the solid support.

According to a second embodiment of the present invention, the formation of IAA can be induced through the addition of tryptophan to the culture medium during the step of fermentation for preparing the strains, allowing the production of IAA themselves and obtaining a completely natural product. According to this example, the resulting culture broth includes the strains ($C_3$ or $M_3$) and IAA which was produced directly by the strains. The broth can be adsorbed directly in the solid support including the IAA produced during the fermentation.

The present invention provides a process for producing biological fertilizers, said process comprising the following steps:

a) Culturing microorganisms $C_3$ and $M_3$.
b) Immobilizing in solid matrices.
c) Drying.

According to the process, step c) consists of drying the solid matrix. This step is the main step of the improved method.

According to the state of the art, separately drying microorganisms and nutrients in solid matrices is well known; the temperatures drying are 80° C. and 200° C., respectively. In fact, a high temperature is required to reduce the moisture content of the solid matrix, for example, zeolite. The acceptable moisture content must be comprised between 4 and 8%, although a lower moisture content would be desirable.

In fact, it is known that when a microorganism is bound to a matrix, the lower the temperature of the drying air stream the greater the survival, the maximum drying temperature allowed in the present case being 80° C., since higher temperatures of the drying stream induce death of the microorganism.

The limits and conditions mentioned above according to the state of the art are surprisingly overcome by the method described according to the present invention. The improvement in the drying is essentially based on the fact that in the present invention the drying is carried out in a fluid bed dryer which allows considerably reducing the temperature of the drying air as is considerably increases the contact area.

The step of drying according to the present invention is therefore characterized in that it comprises the dehydration of the solid support adsorbed with the microorganisms and/or nutrients and salts carried out in a fluid bed dryer, which allows considerably reducing the residual moisture of the product operating at a temperature of only 35° C.

BRIEF DESCRIPTION OF THE DRAWINGS

FIG. 1 shows the results of fertilization treatments in plants, obtained with the biological fertilizer according to the present invention.

In addition, FIGS. 2, 3 and 4 show a summary of the results obtained in the different tests conducted in terms of mean weight of the lettuces and the nitrate content in the soils and the leaves.

DETAILED DESCRIPTION OF AN EMBODIMENT

A description of the method for obtaining the object according to the present invention is explained below as an example.

The fluid bed dryer is fed with the mass necessary for its operation and it is operated at a maximum air temperature of 35° C. The product will thus be gradually dried until reaching moisture that will be between 2-5%, preferably 2-3%, more preferably 2-2.5%, which is the moisture value of the finished product.

The process of immobilizing and adsorbing the nutrients in a single step and drying at maximum temperatures of 35° C. has allowed increasing the stability and effectiveness of the product, which preserves its activity, without significant losses in storage, for at least two years at temperatures of up to 35° C. Its plant growth stimulating activity has been verified for over two years, preserving its initial properties. In its field application, it has proven to be highly effective for colonizing roots of different crops and in different types of soils, as well as having proven the growth stimulating effect and the general nutrition effect of the plants in the tests conducted.

It has also been verified by means of field testing that this method allows eliminating chemical fertilization and produces a considerable improvement in the structure of the soil.

The improvement described above relating to the method for producing the biological fertilizer has several advantages with respect to the process according to the prior state of the art. Lower temperatures and moisture contents make the fertilizer more stable and allow it to remain active for at least two or three years.

The new method of production of the biological fertilizer according to the present invention provides a solution to the technical and industrial problems described above. Furthermore, said method according to step a) has another advantage in the use thereof as a culture medium for the production of the mentioned strains of tomato paste as a carbon source and animal skin collagen hydrolysate for use in fertilizing as an organic nitrogen source with which high cell counts are reached in 24-36 hours of fermentation for both strains. In addition, the introduction of L-tryptophan in the culture medium causes high amounts of auxins to be produced during fermentation, which will later be passed on to the end product, conferring to it an additional root penetration effect from its application. The culture medium is very cost-effective, and more importantly, high cell counts of the order of $10^9$-$10^{10}$ cells×$mL^{-1}$ are reached in both cases. This medium has also been tested with similar results in the culture of strains of other genera of bacteria and fungi isolated by the authors.

The presence of L-tryptophan in the growth medium of the phase of fermentation provides an immediate source for producing IAA by microorganisms $C_3$ and $M_3$.

Furthermore, according to the present method, step b) has another advantage which consists of the immobilization of cells, salts and nutrients in the same solid matrix.

This process is carried out simultaneously and by spraying the solid with the fermentation broths and the solutions of nutrients, following a sequential scheme. In order to carry out this phase, a solid mixer is used which has an accessory which allows spraying liquids as they are mixed and homogenized. The mixer is loaded with zeolite and phosphorus rock and the process of mixing is carried out for 5-10 minutes. Then, and maintaining the mixer in motion, the broths of cells are added in a sequential order, first $M_3$ and then $C_3$. The process of adsorption of the nutrients is carried out using the following raw materials and proportions upon finishing and with the mixer in motion in order to obtain a homogenous wet solid:

| Salt | Concentration | Volume × 100 kg of solids |
|---|---|---|
| $(NH_4)_2SO_4$ | 550-650 g/L | 3.5-4.0 L of solution |
| $K_2HPO_4$ | 500-600 g/L | 0.8-1.2 L of solution |
| $Zn(NO_3)_2 \cdot 4H_2O$ | 100-150 g/L | 0.1-0.2 L of solution |
| $MnSO_4 \cdot H_2O$ | 100-150 g/L | 0.1-0.2 L of solution |
| $CuSO_4 \cdot 5H_2O$ | 10-40 g/L | 0.03-0.06 L of solution |
| $FeSO_4 \cdot 7H_2O$ | 10-40 g/L | 0.03-0.06 L of solution |

Without stopping the mixer, each of the solutions described above is sprayed sequentially and in the same order in which they are described. It is mixed well for 15-30 minutes in order to obtain a homogenous wet solid.

This new improved step reduces the process time and allows obtaining a solid matrix containing the components of the invention. This advantage is very important, since the solid support can be subjected to a single step of drying, thus preventing the need to carry out at least three different steps of drying for the different solid supports with different components.

The main advantage of the method for obtaining the product according to the present invention is the new step of drying. Said new step of drying could be carried out in solid supports according to the prior state of the art, and also in solid supports obtained according to a new aspect, i.e., the possibility of immobilizing both strains $C_3$ and $M_3$ as well as the nutrients and any other component in the solid matrix at the same time and in a single step of the process.

Therefore, according to the present invention the biological fertilizer can be produced according to any process herein described, and the new process can be used for producing any product of the type described above.

EXPERIMENTAL SECTION

The following examples serve to illustrate the principles and methodologies through which all the biological fertilizers are obtained. These examples serve to illustrate the principles and methodologies of the present invention, but they do not limit the scope thereof.

Example 1

Propagation of Strains *Azospirillum brasilense* $M_3$ and *Pantoea dispersa* $C_3$ A blister of the preserved isolate of strain $M_3$ is taken, is seeded on Congo Red medium plates (Rodríguez Cáceres, 1982) and is incubated at 30° C. for 72 hours in order to verify its purity. An inoculum is prepared from this plate for the fermenter, a portion of the culture being taken with a loop, 3 2000-mL Erlenmeyer flasks are each inoculated with 750 mL of tomato medium without L-tryptophan and are incubated under stirring at 30° C. for 14-16 hours. After this time, the content of the flask, which is in exponential phase, is inoculated in a Braun Biotech BIOSTAT® C 30 L fermenter with 18 L of tomato medium without L-tryptophan. It is cultured for 8-10 hours and when it has reached high cell concentration and is still in exponential phase, it is inoculated in a Braun Biotech BIOSTAT® D 300 L fermenter with 200 L of tomato medium. The fermentation is carried out for 24-36 hours at a stirring rate of 200 rpm, and at an aeration of 50 L×min$^{-1}$ (0.25 vvm) and at a temperature of 30° C. The pH is left to vary freely and at the end had a value of 6.5. A concentration of 9.4×10$^9$ cells×mL$^{-1}$ was reached and the final concentration of IAA was 120 mg×L$^{-1}$. The specific growth rate in exponential phase (μ) was 0.28 h$^{-1}$.

As illustrated above, strain $C_3$ followed the same fermentation scheme. The purity of the culture was verified in MacConkey medium (OXOID 1981) and the inoculum was incubated in an orbital agitator for 12 hours. The culture was carried out in the BIOSTAT® D fermenter for 24-36 hours at a stirring rate of 300 rpm, and an aeration of 100 L×min$^{-1}$ (0.5 vvm) and at a temperature of 30° C. The pH is also left to vary freely and at the end had a value of 6.7. A concentration of 1.12×10$^{10}$ cells×mL$^{-1}$ was reached and the final concentration of IAA was 50 mg×L$^{-1}$. The specific growth rate in the exponential phase for this strain was μ=0.52 h$^{-1}$.

Tomato medium:

| Component | g |
|---|---|
| Tomato paste | 36.00 |
| K$_2$HPO$_4$ | 3.30 |
| KH$_2$PO$_4$ | 2.75 |
| NH$_4$CL | 0.84 |
| Collagen hydrolysate | 5.00 |
| Yeast extracts | 0.75 |
| Tryptophan | 0.2 |
| H$_2$O$_{(qsf)}$ | 1 L | pH = 7.0
Sterilization at 121° C. for 30 minutes

Example 2

Cell Immobilization and Loading of Nutrients

A plow mixer having a sprayer is used to carry out this process and the following raw materials are used:

97.5 Kg of zeolite 2.5 Kg of phosphorus rock 3.6 L of $M_3$ broth 3.6 L of $C_3$ broth The mixer is loaded with zeolite and phosphorus rock and the process of mixing is carried out for 5-10 minutes. Then, and maintaining the mixer in motion, the broths of cells are sprayed in sequential order, first $M_3$ and then $C_3$. The process of adsorption of the nutrients is carried out using the following raw materials and proportions upon finishing and with the mixer in motion in order to obtain a homogenous wet solid:

| | | |
|---|---|---|
| (NH$_4$)$_2$SO$_4$ | 590 g/L | 3.83 L of solution |
| K$_2$HPO$_4$ | 550 g/L | 1.05 L of solution |
| Zn(NO$_3$)$_2$•4H$_2$O | 122.5 g/L | 0.15 L of solution |
| MnSO$_4$•H$_2$O | 120 g/L | 0.15 L of solution |
| CuSO$_4$•5H$_2$O | 24 g/L | 0.05 L of solution |
| FeSO$_4$•7H$_2$O | 24 g/L | 0.05 L of solution |

Without stopping the mixer, each of the solutions described above is sprayed sequentially and in the same order in which they are described, passing a small amount of water between each nutrient to clean the conduits. A total of 7.2 L were added in this phase. It is mixed well for 15-30 minutes in order to obtain a homogenous wet solid.

The zeolite with the phosphorus rock was moistened with 14.4 L of total liquid, which was completely absorbed without there being any left-over liquid.

Example 3

Drying

The fluid bed dryer is fed with the mass necessary for its operation and it is operated at a maximum air temperature of 35° C. The product will thus be gradually dried until reaching a final moisture that will be between 2-3% which is the moisture value of the finished product.

The cell viability of this product will be verified periodically in Congo Red medium (Rodríguez Cáceres, 1982) for *Azospirillum brasilense* $M_3$ and in MacConkey medium (OXOID 1981) for *Pantoea dispersa* $C_3$, finding that over 90% of the activity thereof is preserved over more than two years of storage at temperatures not greater than 35° C. It is obvious that the combined process of immobilization and adsorption of nutrients, which allows greater saturation of the support, and the drying temperature of 35° C., which is much lower with respect to the drying temperature according to the prior state of the art, and which acts very favorably on cell survival in the process of storing the product, have allowed considerably increasing the effectiveness of the useful life of the product, as can be seen in FIG. 1.

This figure particularly shows that the lettuce treated with the biological fertilizer with over two years of storage maintains a higher natural growth standard compared with the control, which did not receive any treatment. The gray bar in the graph represents the fresh weight of the green part of plants (FWG) and the black bar indicates the fresh weight of the root (FWR) of lettuce resulting from a greenhouse bioassay in pots and on peat as a substrate. The bar graph shows that the fertilizer obtained by this method maintains greater stability and activity for over two years. As can be seen, after 2 and a half years the product still preserved over 90% of its effectiveness.

Example 4

Evaluation of Agricultural Advantages

In order to show that the product is more active compared to chemical fertilizers, several experimental conditions have been investigated. For example, different cultures were tested in field conditions and the results obtained were very satisfactory. The lettuce crop, in particular, was tested in field conditions to find the variability between soils, varieties and irrigation systems.

In all these tests, chemical fertilization was completely replaced, obtaining excellent results in terms of the crop harvest and in terms of the nitrate content both in the leaves and in the soils. The results of the size distribution of the lettuces in one of the tests conducted are shown in Table 1. As can be seen, a better size distribution (more suitable sizes) of commercial interest was achieved with the use of the product for the purposes of the crop harvest because a much larger proportion of C-9 and C-10 was achieved with the fertilizer than in traditional cultivation treated with chemical fertilization.

TABLE 1

Commercial size distribution in the Águilas test.
% SIZE DISTRIBUTION

| SIZES | Fertilizer | CULTURE USED |
|---|---|---|
| C-9 | 16% | 28% |
| C-10 | 57% | 68% |
| C-12 | 27% | 4% |

FIG. 2 shows the effects of the treatment in the growth of the plant, measured as average weight in grams. The gray bar of the graph represents the biological fertilizer according to the present invention, and the black bar indicates the control used. It is observed that in particular experimental conditions the weight of the lettuce treated with the fertilizer is greater than or comparable to that of the lettuce treated with chemical fertilizer. In fact, it is observed that despite not using chemical fertilization, the results obtained are similar and even greater than those of the culture used.

FIGS. 3 and 4 show a reduction of the concentration of nitrates and environmental pollutants in the soil (FIG. 3) and in the leaves (FIG. 4). It is obvious that the use of biological fertilizer significant reduces the presence of nitrates and/or pollutants both in the soil and in the leaves compared to chemical fertilizers.

In FIG. 3, it can furthermore be concluded that environmental pollution due to nitrates, phosphates and other chemical fertilizers is drastically reduced by means of using this biofertilizing product. Since no type of chemical fertilization is added, the washout effect of these salts from the soils is virtually eliminated. The nitrate content in leaves (FIG. 4) was furthermore reduced considerably, making the product much healthier.

The invention claimed is:

1. A biological fertilizer and plant growth stimulator comprising:
   a.—a pure culture of strain $C_3$ of the *Pantoea dispersa* species deposited in the Spanish Type Culture Collection (CECT) with CECT number 5801,
   b.—a pure culture of strain M3 of the *Azospirillum brasilense* species deposited in the CECT with CECT number 5802,
   both immobilized in a solid support; and
   c.—indole-3-acetic acid (IAA), or a promoter of indole-3-acetic acid.

2. The biological fertilizer according to claim 1, wherein said strain referred to as $C_3$ is capable of producing in tomato medium indole-3-acetic acid in concentrations of the order of 80-120 mg×L$^{-1}$.

3. The biological fertilizer according to claim 1, wherein said strains $C_3$, $M_3$ and said indole-3-acetic acid are immobilized in said solid support.

4. The biological fertilizer according to claim 3, wherein said solid support is formed by natural zeolites.

5. The biological fertilizer according to claim 3, wherein said solid support is selected from the group consisting of clay, vermiculite, perlite, sepiolite, kaolin, diatomaceous earth, and natural zeolite.

6. The biological fertilizer according to claim 1, comprising a concentration of indole-3-acetic acid of the order of 50-120 mg×kg$^{-1}$ of product.

7. The biological fertilizer according to claim 4, wherein the natural zeolites have been loaded with salts and have the following composition: total nitrogen ($NH_4^+$): 0.3-0.5%, potassium ($K_2O$): 0.10-0.25%, phosphorus ($P_2O_5$): 0.50-0.75%, zinc ($Zn^{2+}$): 85-110 ppm, iron ($Fe^{2+}$): 600-800 ppm, manganese ($Mn^{2+}$): 250-300 ppm and copper ($Cu^{2+}$): 10-20 ppm.

8. The biological fertilizer according to claim 1, wherein the fertilizer behaves as a slow release system for releasing cells or nutrients.

9. The biological fertilizer according to claim 1, wherein the fertilizer has a moisture content comprised between 2-5%.

10. The biological fertilizer according to claim 1, wherein the fertilizer has a moisture content comprised between 2-3%.

11. The biological fertilizer according to claim 1, wherein the fertilizer has a moisture content comprised between 2-2.5%.

12. The biological fertilizer according to claim 1, wherein said promoter of the indole-3-acetic acid is L-tryptophan.

13. A method for the preparation and production of a biological fertilizer, said biological fertilizer comprises strains of *Azospirillum brasilense* strain $M_3$ (CECT-5802), *Pantoea dispersa* strain $C_3$ (CECT-5801) and indole-3-acetic acid (IAA), or a promoter of indole-3-acetic acid, comprising the steps of culturing said strains, immobilizing them on solid matrices and drying said matrices, characterized in that said step of drying is carried out in a fluid bed dryer at a temperature of less than 35° C., with continuous drying and air flow, obtaining said biological fertilizer with a moisture content between 2-5%.

14. The method according to claim 13, wherein said moisture content is comprised between 2-3%.

15. The method according to claim 13, wherein said moisture content is comprised between 2-2.5%.

16. The method according to claim 13, wherein said step of culturing said strains comprises the fermentation of said strains in a growth medium with L-tryptophan added thereto.

17. The method according to claim 13, wherein said step of immobilization is carried out by the adsorption of strains and nutrients in the same solid matrix.

18. The method according to claim 17, wherein said solid matrix is zeolite.

19. The method according to claim 13, wherein said step of immobilizing is carried out by the adsorption of strains, salts and nutrients to different solid matrices.

20. The method according to claim 19, wherein said solid matrices are zeolites.

21. A biological fertilizer obtained according to claim 13.

22. A biological fertilizer obtained according to claim 16.

* * * * *